US00PP34633P2

(12) United States Plant Patent
Smit

(10) Patent No.: US PP34,633 P2
(45) Date of Patent: Oct. 4, 2022

(54) ***PEPEROMIA* PLANT NAMED 'EC-PEPE-2110'**

(50) Latin Name: *Peperomia argyreia*
Varietal Denomination: EC-PEPE-2110

(71) Applicant: Eden Collection, BV, Sappemeer (NL)

(72) Inventor: Obed Smit, Sappemeer (NL)

(73) Assignee: Eden Collection B.V.

( * ) Notice: Subject to any disclaimer, the term of this patent is extended or adjusted under 35 U.S.C. 154(b) by 0 days.

(21) Appl. No.: 17/677,526

(22) Filed: Feb. 22, 2022

(51) Int. Cl.
*A01H 5/12* (2018.01)
*A01H 6/00* (2018.01)

(52) U.S. Cl.
USPC ..... Plt./373

(58) Field of Classification Search
USPC ..... Plt./373, 263.1

CPC ... A01H 5/12; A01H 5/00; A01H 5/02; A01H 6/00

See application file for complete search history.

(56) References Cited

PUBLICATIONS

CPVO Register 4.1.45, retrieved on Mar. 24, 2022 at https://online.plantvarieties.eu/publicConsultationDetails?registerId=20212660&denomination=ec%20pepe%202110, 3 pp. (Year: 2022).*

* cited by examiner

*Primary Examiner* — June Hwu
(74) *Attorney, Agent, or Firm* — Cassandra Bright

(57) ABSTRACT

A new and distinct cultivar of *Peperomia* plant named 'EC-PEPE-2110' is disclosed, characterized by unique silver-grey-blue upper leaf color. Foliage has very narrow, dark green veins that contrast beautifully with its silver-grey-blue color. The new variety is a *Peperomia*, typically used as an ornamental plant.

3 Drawing Sheets

Latin name of the genus and species: *Peperomia argyreia*.
Variety denomination: 'EC-PEPE-2110'.

BACKGROUND OF THE INVENTION

The new cultivar is a product of a naturally occurring branch mutation of *Peperomia argyreia* 'EC-PEPE-2008', U.S. Plant Pat. No. 32,940. 'EC-PEPE-2110' was found and selected by the inventor, Obed J. Smit, in 2019, at a commercial greenhouse in Sappemeer, the Netherlands.

Asexual reproduction of the new cultivar 'EC-PEPE-2110' by terminal cuttings was first performed in Sappemeer, the Netherlands at the same nursery in May 2019, and has shown that the unique features of this cultivar are stable and reproduced true to type through successive generations.

SUMMARY OF THE INVENTION

The cultivar 'EC-PEPE-2110' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'EC-PEPE-2110'. These characteristics in combination distinguish 'EC-PEPE-2110' as a new and distinct *Peperomia* cultivar:

1. Unique silver-grey-blue upper leaf color.
2. Very narrow, dark green veins that contrast beautifully with the silver-grey-blue leaf color.

PARENT COMPARISON

Plants of the new cultivar 'EC-PEPE-2110' are similar to plants of the parent, *Peperomia argyreia* 'EC-PEPE-2008' in most horticultural characteristics, however, plants of the new cultivar 'EC-PEPE-2110' differ from in the following characteristics:

1. Upper leaf color of the new variety is silver-grey-blue, while the upper leaf color of the parent is silver-grey.
2. The new variety has very narrow, dark green veins that contrast with the silver-grey-blue upper leaf color. The parent variety has much wider dark green veins that contrast with its silver-grey leaf color.

COMMERCIAL COMPARISON

Plants of the new cultivar 'EC-PEPE-2110' are similar to plants of the commercial variety *Peperomia polybotrya* 'Raindrop', unpatented. However, plants of the new cultivar differ in the following characteristics:

1. Upper leaf color of the new variety is silver-grey-blue, while the leaf color of this comparator is fully green.
2. Leaves of the new variety are formed around the leaf stem, while leaves of this comparator are incised at the leaf stem.
3. Plants of the new variety have a rosette shape, while plants of this comparator grow more upward.

Plants of the new cultivar 'EC-PEPE-2110' are similar to plants of the species *Peperomia argyreia*. However, plants of the new cultivar differ in the following characteristics:

1. Plants of the new variety are more compact and dense than plants of this comparator.
2. Upper leaf color of the new variety is silver-grey-blue, while the upper leaf color of this comparator is silver-grey.
3. The new variety has very narrow, dark green veins that contrast with the silver-grey-blue upper leaf color. *Pep-*

*eromia argyreia* has much wider dark green veins that contrast with its silver-grey leaf color.

BRIEF DESCRIPTION OF THE PHOTOGRAPHS

The accompanying photograph in FIG. 1 illustrates in full color a typical plant of 'EC-PEPE-2110' grown in a greenhouse. The plant is approximately 25 weeks of age.

Figure 1:
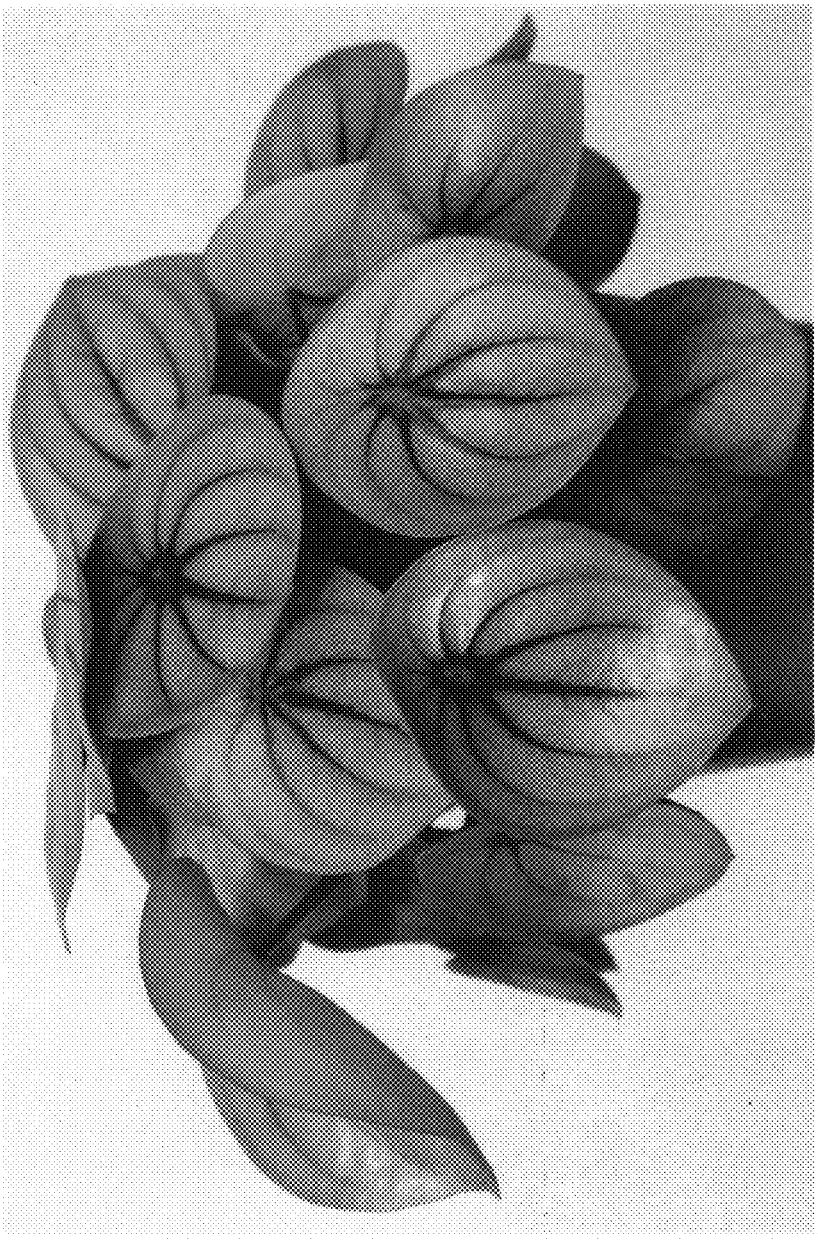
Figure 2:
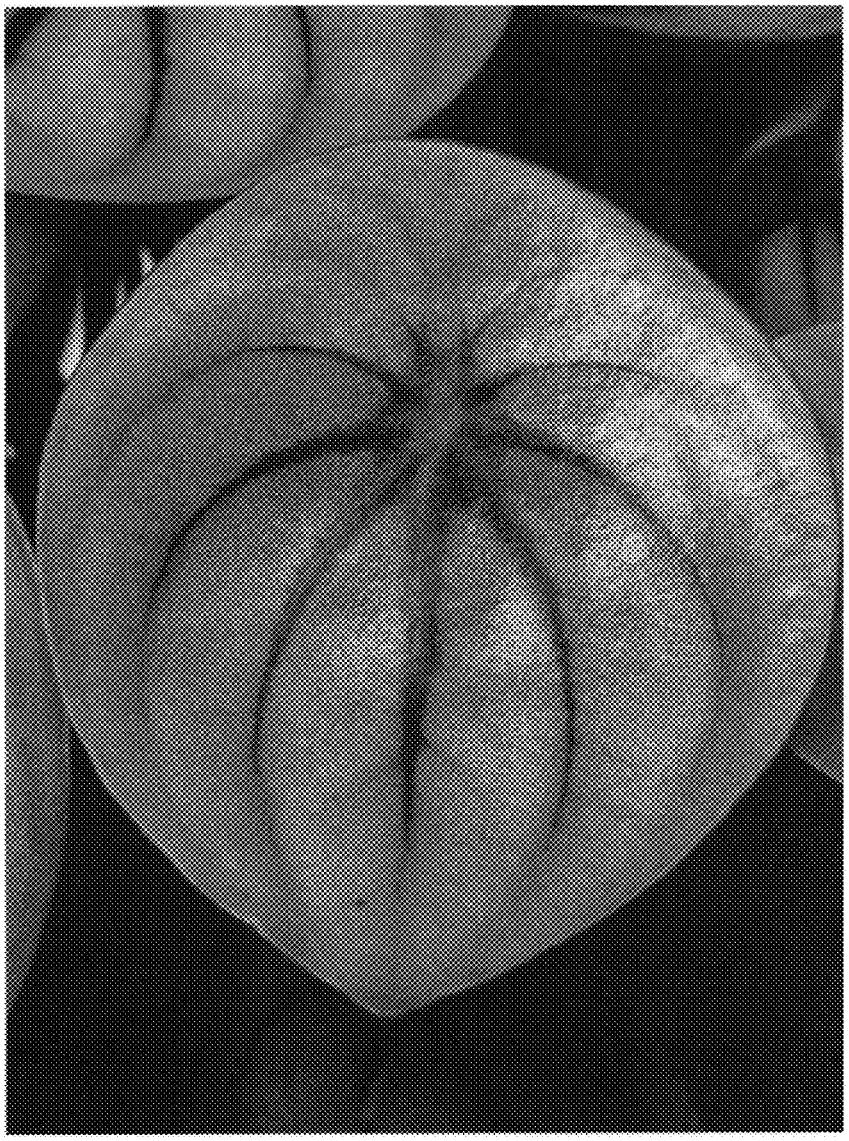
FIG. 2 illustrates a close up of the foliage.
Figure 3:
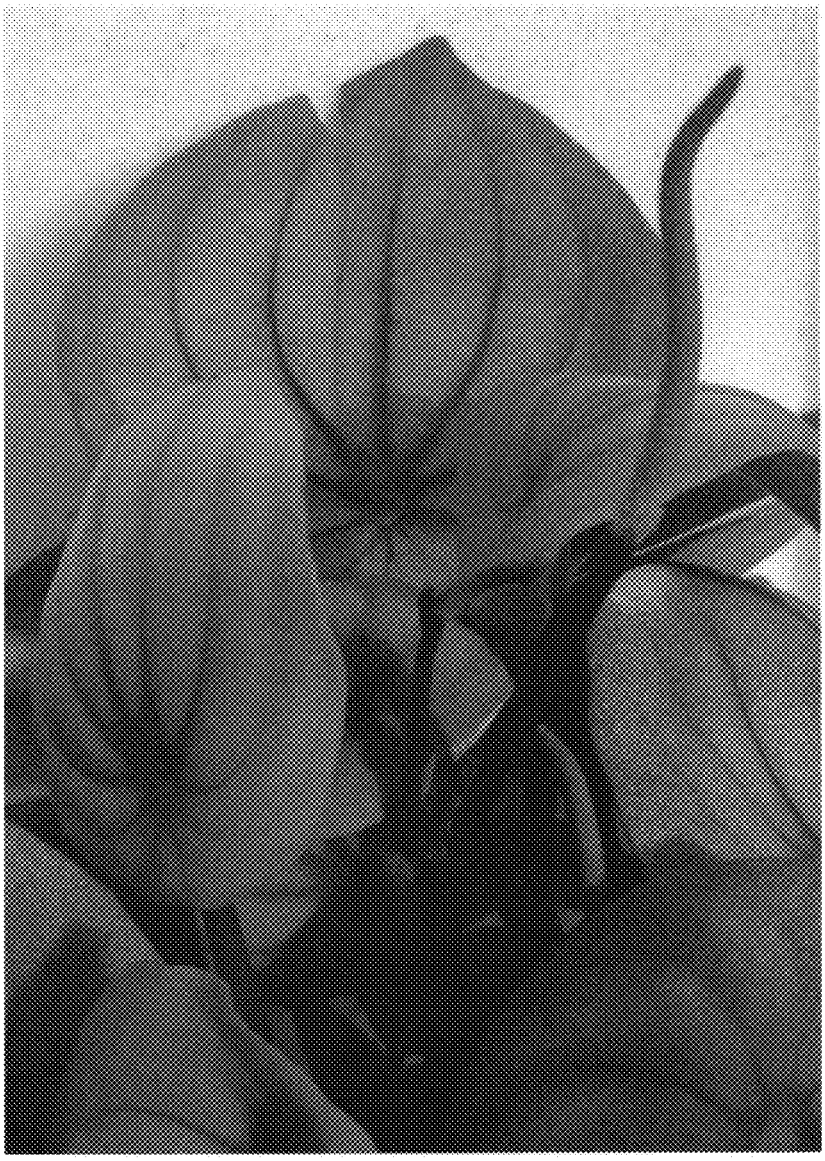
FIG. 3 illustrates a close up of the inflorescence.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2015 except where general terms of ordinary dictionary significance are used. The following observations and measurements describe 'EC-PEPE-2110' plants at 8 months of age, grown in a greenhouse in Sappemeer, the Netherlands during October. The growing temperature ranged from 18° C. to 20° C. at night to 19° C. to 22° C. during the day. Measurements and numerical values represent averages of typical flowering types.

Botanical classification: *Peperomia argyreia* 'EC-PEPE-2110'.

PROPAGATION

Time to initiate roots: About 19 days at 21° C. in summer, 21 days at 21° C. in winter.

Time to produce rooted cutting: About 80 days at 21° C. in summer.

Description of roots: Fibrous, fine, fairly dense, herbaceous, freely branching. Brown in color, not accurately measured with R.H.S. chart.

PLANT

Plant type: Perennial potted plant.

Plant shape: Flattened globular.

Growth habit: Rosettes of leaves, forming very short, thick stems.

Plant spread: Approximately 33.4 cm.

Height: 15.1 cm to top of foliar plane.

Growth rate: Moderate.

Plant vigor: Moderate to high.

Age of plant described: Approximately 8 months.

Branching habit: Leaves in rosettes, eventually forming short, thick stems.

Pinching: Pinching not required.

Number of primary (main) branches per plant: Average 7.

Number of secondary (lateral) branches per plant: None.

Main branches:

*Length*.—Average: 2.5 cm.

*Diameter*.—Average: 0.7 cm.

Internode length: Average: 0.3 cm.

Appearance and shape: Succulent, thick and rounded.

Luster: Moderately glossy.

Aspect/angle from vertical: Average angle: 20°.

Strength: Moderately strong.

Color:

*Developing*.—RHS Greyed-Orange 176A.

*Mature*.—RHS Greyed-Orange to Greyed-Red, slightly darker than a blend of 176A and 178A.

*At internodes*.—RHS Greyed-Orange to Greyed-Red, slightly darker than a blend of 176A and 178A.

*Pubescence*.—None.

*Plant fragrance*.—None.

FOLIAGE

Leaf:

*Arrangement*.—Alternate, single.

*Quantity*.—Average 6 per lateral branch.

*Average length*.—10.2 cm.

*Average width*.—8.7 cm.

*Shape of blade*.—Broad ovate, perfoliate.

*Aspect*.—Slightly concave.

*Apex*.—Broad short apiculate.

*Base*.—Rounded.

*Margin*.—Entire.

*Texture of top surface*.—Glabrous, smooth, moderately leathery, velvety.

*Texture of bottom surface*.—Glabrous, smooth, moderately leathery.

*Pubescence*.—None.

*Luster, upper side*.—Glossy.

*Luster, under side*.—Slightly glossy.

*Color*.—Young foliage upper side: RHS Yellow-Green 145A, veined darker, 144A. Young foliage under side: RHS Yellow-Green, blend of 144D and 145B; veined darker, 144A. Mature foliage upper side: RHS Greyed-Green, blend of 188A and 188B, with a conspicuous, silvery shine, impossible to measure with R.H.S. chart. Area around veins RHS Green 139A, narrower towards margins and top. Mature foliage under side: RHS Yellow-Green 148D.

*Venation*.—Pattern: Parallel, slightly furrowed. Venation color upper side: RHS Green 137A. Venation color under side: RHS Yellow-Green 146C.

*Petiole*.—Average Length: 9.5 cm. Diameter: 0.4 cm. Texture: Glabrous, smooth. Luster, upper side: Slightly glossy. Luster, under side: Moderately glossy. Strength: Low. Color, upper side: RHS Greyed-Purple 183A, very slightly tinged Brown 200B; moderately covered with lenticels, average length: 2 mm; average width: 0.75 mm; colored RHS Yellow-Green 147D; less dense present toward distal end. Color, under side: RHS Greyed-Purple 183A, very slightly tinged Brown 200B; moderately covered with lenticels, average length: 2 mm; average width: 0.75 mm; colored RHS Yellow-Green 147D; less dense present toward distal end.

FLOWER

Inflorescence:

*Arrangement*.—Axillary spike, solitary or in pairs.

*Inflorescence type and form*.—Spike.

*Inflorescence height*.—Average: 8.4 cm (excluding peduncle).

*Inflorescence diameter*.—Average: 0.3 cm.

*Quantity of flowers per inflorescence*.—Average: About 1,250 individual flowers per spike.

*Quantity of flower and buds per plant*.—Average: approx. 4,300 individual flower buds per plant. Typically 1 to 3 flowering spikes per plant.

*Natural flowering season*.—Flowering can begin anytime under greenhouse conditions.

Flower bud:

*Flower bud length*.—Individual buds measure approx. 0.4 mm.

*Flower bud diameter*.—Individual buds measure approx. 0.4 mm.

*Flower bud shape*.—Flattened, circular.

*Flower bud texture*.—Glabrous, smooth, slightly velvety.

*Flower bud luster*.—Slightly glossy.

*Flower bud color*.—Yellow-green, very difficult to measure due to small size, but close to 146C, slightly tinged greyed-purple; very difficult to measure due to small size, but close to 184A.

Flower:

*Flower type and form*.—Individual flowers are very small and consist of 1 bract, 2 stamens and a single pistil.

*Fragrance*.—No fragrance.

*Flower shape*.—Rotate, consisting of 1 bract, 2 stamens and 1 pistil only; no petals nor sepals present.

*Flower height* (*vertical*).—Average: 1.25 mm.

*Flower diameter* (*horizontal*).—Average: 0.8 mm.

*Flower length* (*depth*).—Average: 0.8 mm.

*Flower longevity on plant*.—Average: one month.

*Persistent of self-cleaning?*.—Self-cleaning.

Peduncles:

*Length*.—Average: 3.8 cm (from lowest individual flower to base).

*Diameter*.—Average: 2.0 mm.

*Peduncle angle to lateral branch axis*.—Average angle: 20°.

*Strength*.—Weak.

*Texture*.—Glabrous, smooth.

*Luster*.—Moderately glossy.

*Color*.—Near RHS Greyed-Purple 185A.

Pedicels: No pedicels present, individual flowers sessile.

Floral bracts: A single bract is present, orbicular, average length and width: 0.5 mm, colored yellow-green; very hard to measure with R.H.S. Chart due to small size but close to 146D.

Reproductive organs:

*Number of stamen per flower*.—Average: 2.

*Filament length*.—Average: 0.5 mm.

*Filament color*.—Near RHS Yellow-Green 146D.

*Anther shape*.—Ovate.

*Anther length*.—Average: 0.2 mm.

*Anther width*.—Average: 0.15 mm.

*Anther color*.—Near RHS Yellow-Green 145D.

*Amount of pollen*.—Low.

*Pollen color*.—Near RHs White 155A.

*Pistil number* (*per flower*).—Average: 1.

*Pistil length*.—Average: 0.2 mm.

*Stigma shape*.—Club-shaped.

*Stigma length*.—Average: 0.2 mm.

*Stigma diameter*.—Average: 0.2 mm.

*Stigma color*.—Near RHS Green-White 157A.

*Style length*.—No style visible.

*Ovary color*.—Near RHS Yellow-Green 146D.

OTHER CHARACTERISTICS

Seeds and fruits: None observed to date.

Disease/pest resistance: No increased nor decreased resistance nor susceptibility to normal diseases and pests of *Peperomia argyreia* has been observed.

Temperature tolerance: Tolerates temperatures up to 40° C. Hardy to USDA zones 10 to 12. Moderate tolerance to rain. High tolerance to wind.

What is claimed is:

1. A new and distinct cultivar of *Peperomia* plant named 'EC-PEPE-2110' as herein illustrated and described.

* * * * *